United States Patent [19]

Sessions et al.

[11] 4,353,373
[45] Oct. 12, 1982

[54] EKG ELECTRODE AND PACKAGE

[75] Inventors: Robert W. Sessions, Burr Ridge; Jerome Jeslis, Chicago; Richard A. Rodzen, Bolingbrook, all of Ill.

[73] Assignee: Ferris Manufacturing Corp., Burr Ridge, Ill.

[21] Appl. No.: 141,057

[22] Filed: Apr. 17, 1980

[51] Int. Cl.³ .............................................. A61B 5/04
[52] U.S. Cl. .................................................... 128/641
[58] Field of Search ............................... 128/639–641, 128/644, 803, 798

[56] References Cited

U.S. PATENT DOCUMENTS

| | | | |
|---|---|---|---|
| 3,085,577 | 4/1963 | Berman et al. | 128/641 |
| 3,151,619 | 10/1964 | Sullivan | 128/640 |
| 3,487,827 | 1/1970 | Edmark | 128/641 |
| 3,701,346 | 10/1972 | Patrick, Jr. et al. | 128/641 |
| 3,805,769 | 4/1974 | Sessions | 128/641 |
| 3,828,766 | 8/1974 | Kresnow | 128/641 |
| 3,989,035 | 11/1976 | Zuehlsdorff | 128/641 |
| 4,029,086 | 6/1977 | Corasanti | 128/641 |
| 4,034,854 | 7/1977 | Bevilacqua | 128/641 X |
| 4,067,322 | 1/1978 | Johnson | 128/641 |
| 4,155,354 | 5/1979 | Rasmussen | 128/640 |

Primary Examiner—Lee S. Cohen
Attorney, Agent, or Firm—Hill, Van Santen, Steadman, Chiara & Simpson

[57] ABSTRACT

An improved EKG electrode and package has a rectangularly shaped foam body member which is sealingly adhered to a first side of a plastic liner. A gelled foam disk is centrally attached to the same side of the foam body member. A plastic sealing cap covering the gelled disk is attached to the other side of the polyethylene liner material. An electrical contact is centered with respect to the disk and passes through the foam body member. The inventive method includes the steps of punching a centrally located hole in the foam body member, attaching an electrical contact through said hole, applying a foam disk to the body member, adjacent one side of the electrical contact, injecting gel into said disk, and sealingly applying a formed plastic cap over the gelled disk.

3 Claims, 9 Drawing Figures

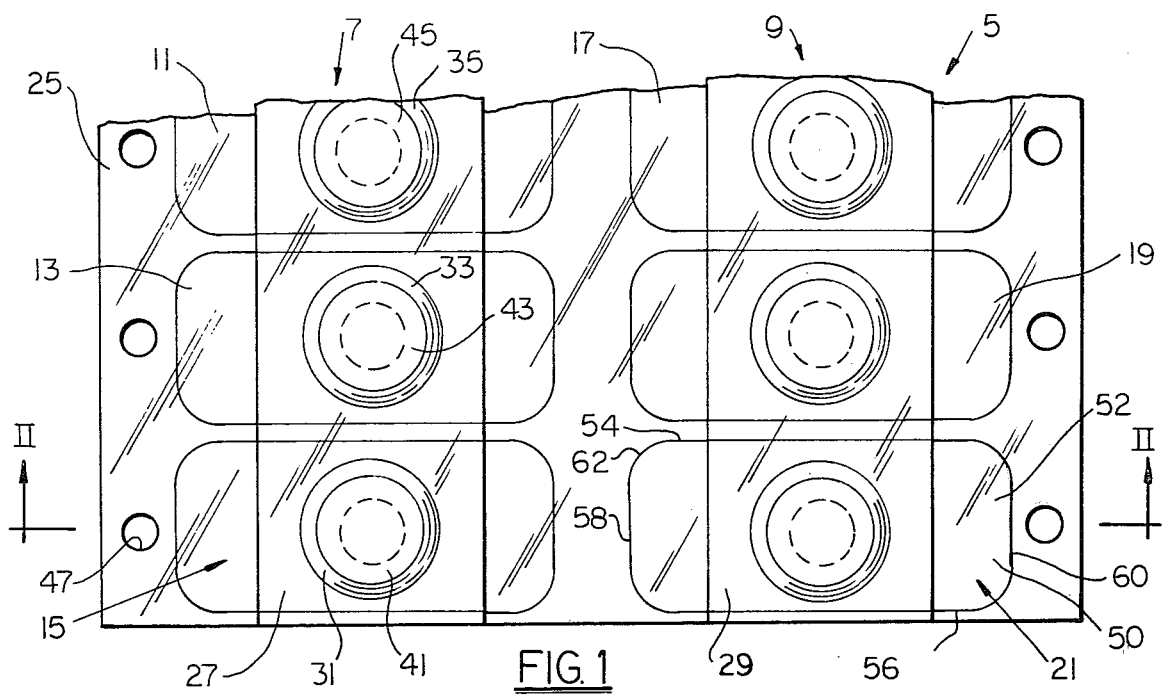
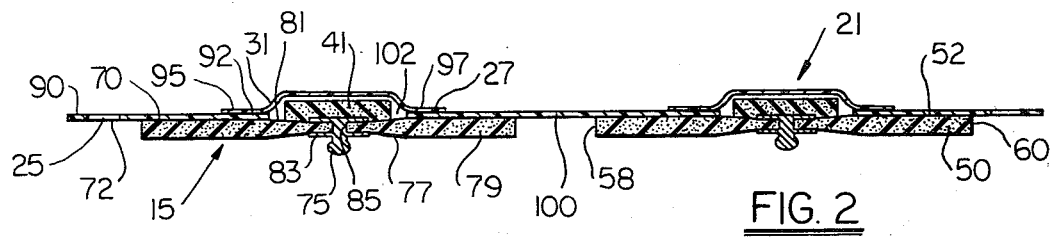
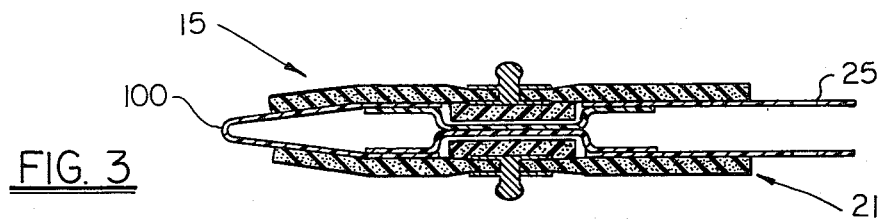
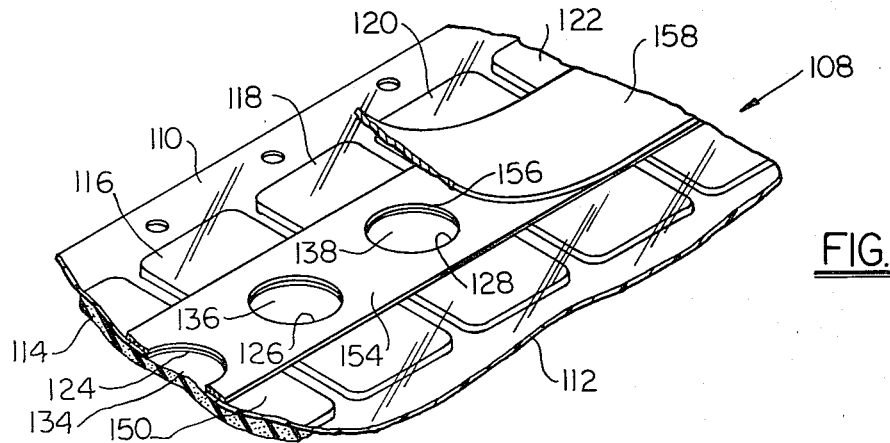

EKG ELECTRODE AND PACKAGE

BACKGROUND OF THE INVENTION

1. Field of the Invention

The invention pertains to EKG Electrodes and a method of making same.

2. Prior Art

EKG electrodes are well known in the prior art. Examples are found in U.S. Pat. Nos. 3,805,769 and 4,034,854. Many of the prior art EKG electrode structures, however, have suffered from the disadvantage that their shelf life has been measured in only weeks. One of the problems has been that the seal covering the disk of gel-impregnated foam in the electrode, which is adjacent the electrical contact, has not been adequate to retain the moisture in the gel for more than a few weeks of shelf life. Additionally, the prior art electrode structures have suffered from the defect that due to their size and circular shape, the number of them which could be used simultaneously on a person with a small chest has been limited.

SUMMARY OF THE INVENTION

Our present invention comprises an improved EKG electrode structure and associated package as well as a method of making same. The improved electrode structure has a rectangularly shaped foam pad with a layer of adhesive along one side thereof. Attached to the same side of the foam pad is a circular foam disk which has been impregnated with a gel. Adjacent the foam disk and extending through the rectangularly shaped foam pad is a metal electrical connector. The package of the electrode is formed with the adhesive side of the foam pad adhered to a thin layer of plastic such as polyethylene. The polyethylene has a circular hole in it through which extends the gelled disk. A plastic cap, polyethylene or MYLAR, is applied over the gelled disk and sticks to a layer of adhesive on the other side of the sheet of polyethylene. The plastic cap which is sealingly attached to the polyethylene base layer results in a very efficient form of packaging which extends the shelf life of the electrode from merely weeks to months.

Our inventive packaging may be formed with two strips of electrodes adhered to the base plastic layer, essentially parallel to one another. The polyethylene base layer may be folded in half, resulting in a very efficient and compact way in which to store the electrodes.

Our inventive method of forming our improved electrode and associated packaging starts with a multi-layer preform with a polyethylene sheet that has a series of holes. A plurality of rectangularly shaped foam pads is adhered to one side of the sheet due to the layer of adhesive on each of the pads. Each pad is centered with respect to a corresponding hole. On the other side of the polyethylene sheet is a layer of adhesive to which is temporarily attached a protective liner which has a series of holes therein. Each hole in the liner corresponds to a hole in the polyethylene sheet. A second liner is sealingly attached to the exposed adhesive on each of the foam pads to cover the series of holes in the foam pads. The method of forming our improved protective packaging along with our improved electrodes includes the steps of removing the second liner from the strip of pre-formed polyethylene material, making a hole through the foam pad essentially centered with respect to the hole in the first liner, applying a metal snap electrode through the hole in the foam pad, applying a centered foam disk to the adhesive layer on each pad adjacent the corresponding hole in the first liner, impregnating each of the foam disks with a gel, removing the first liner and applying a plastic cap over each of the impregnated foam disks. The plastic cap is sealingly adhered to the polyethylene sheet by a layer of adhesive on the polyethylene sheet.

In the above method, twice as many electrodes may be produced essentially simultaneously on a polyethylene or MYLAR sheet which is carrying two strips of rectangularly shaped EKG electrode pads by carrying out the above sequence of steps essentially simultaneously on both sets of electrode pads.

BRIEF DESCRIPTION OF THE DRAWINGS

FIG. 1 is a planar top view showing two rows of electrodes sealed in our inventive package.

FIG. 2 is a sectional view taken substantially along line II—II of FIG. 1.

FIG. 3 is a sectional view showing the package of FIG. 2 folded in half.

FIG. 4 is a perspective view of a fragment of the basic four-layer sheet material out of which our improved electrode and improved packaging material is formed.

DETAILED DESCRIPTION OF THE PREFERRED EMBODIMENTS

Figure 5:
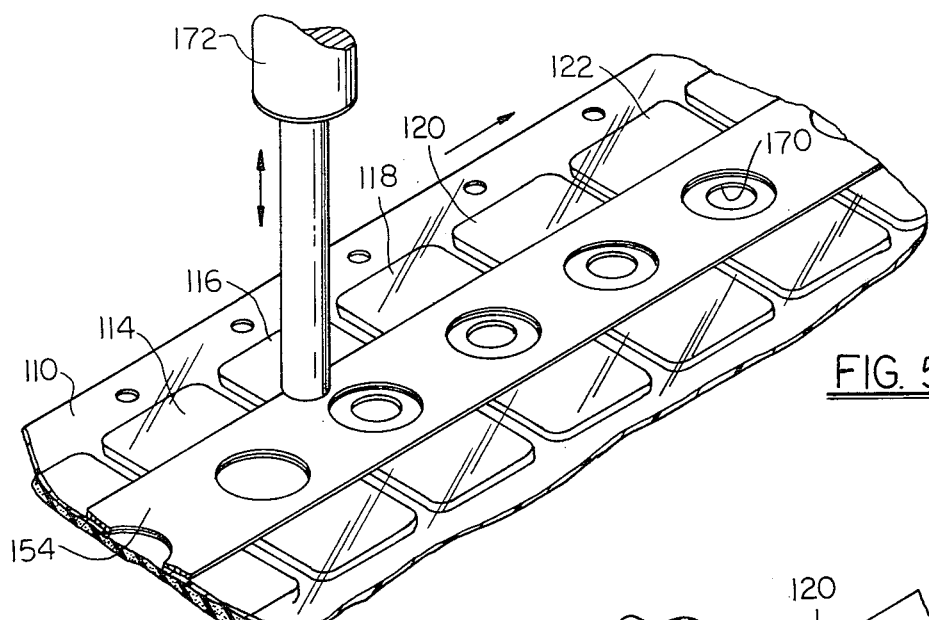
FIG. 5 is a perspective view of a fragment of the basic sheet material with a hole being punched through each EKG electrode pad.

Not by way of limitation, but by way of disclosing the best mode of practicing our invention and by way of enabling one of ordinary skill to practice our invention, there is disclosed in FIGS. 1 through 3 one form of our invention, and in FIGS. 4 through 9 a method of practicing our invention.

FIG. 1 is a planar view of our improved EKG electrodes in associated packaging 5. Two parallel strips 7, 9 of our improved electrodes 11 through 21 are shown packaged and ready for use on a layer of liner material 25. The liner material 25 may be polyethylene or may be a MYLAR material. The MYLAR material is preferred because of its moisture-retaining characteristics. Each of the electrodes 11 through 21 is removably attached to one side of the liner material 25. Attached to the other side of the liner material 25 are two parallel plastic strips 27, 29. The strips 27, 29 are sealingly bonded to the liner material 25. Each of the strips 27, 29 includes a plurality of spaced apart cap members 31, 33, 35 which is formed in the polyethylene or MYLAR strip 27 or 29. Each of the cap members 31, 33 or 35 covers a foam disk such as the disks 41, 43 and 45. The sealing bond between the layer of plastic cover material 27 and the liner material 25 seals the moisture into the gel which has been injected into the foam disks 41 through 45 for a much longer period of time than has heretofore been possible. The moisture is further sealed into the gel due to the fact that each of the electrodes 11 through 15 is sealingly bonded to a lower side of the polyethylene liner sheet 25.

The polyethylene liner 25 is formed with a series of indexing holes 47 therein. Each of the holes 47 is spaced equidistant from an adjacent corresponding hole and may be used for indexing the liner sheet 25 along a manufacturing machine which is forming the package 5.

Each of the electrodes 11 through 21 is identical, and a description of the general shape of the electrode 21 will also describe the remaining electrodes 11 through 19. The electrode 21 is formed from a rectangularly shaped layer of medical foam 50. The layer of foam 50, approximately 1/16" thick, has an adhesive coated upper surface 52, and a pair of elongated spaced apart sides 54, 56. The elongated spaced apart sides 54, 56 are joined by a pair of shorter spaced apart sides 58, 60. Between each pair of sides 54, 58, for example, is a rounded corner 62. The elongated shape of the foam pad 50 makes it particularly suitable for close placement of the electrodes, or for use with persons that have a relatively small chest, such as children.

FIG. 2, a section taken substantially along the line II—II of FIG. 1, shows the structure of details of the packaging and the improved electrodes 5. On the left-hand side of FIG. 2, the electrode 15 which has an upper adhesive surface 70 is sealingly bonded to a lower surface 72 of the polyethylene liner 25. Centrally located with respect to the electrode 5 is a two-part metal contact 75 which extends from an outside surface 77 of the foam layer 79 through to an inside surface 81 of the foam layer 79. Adjacent both the outside surface and the inside surface the metal contact 75 has an annular metal region 83 attached thereto. The metal contact 75 extends through a hole 85 in the foam layer 79. The two-part metal contact 75 when inserted from the top and bottom is pressed against the foam layer 79, compressing it and producing a moisture-resistant seal between the metal contact 75 and the foam material 79.

The gel impregnated disk 41 is sealingly bonded to the layer of adhesive 70 on the upper surface of the foam body 79 of the electrode 15. Additionally, the cap 31 is sealingly bonded to a top surface 90 of the polyethylene liner 25 by a sealing layer 92 which is applied to the top surface 90 of the polyethylene liner 25. The cap 31 is formed with a pair of laterally extending side members 95, 97 which sealingly adhere to the layer of adhesive 92. The electrode 15 is joined to the electrode 21 by a region 100 of the polyethylene liner 25. Except for the lateral displacement with respect to one another, electrodes 15 and 21 are identical.

As shown in FIG. 3, the electrode 15 may be folded over and moved adjacent to the electrode 21 by bending the region 100 of the polyethylene liner 25. The arrangement shown in FIG. 3 produces a very compact way in which the electrodes and associated packaging 5 may be stored on the shelf.

The advantage of the packaging arrangement shown in FIGS. 1 through 3 is that the caps, such as the cap 31 on the plastic strip 27 are sealingly bonded to the liner material 25 very effectively thus trapping the moisture in the gel in the disk 41. Additionally, the foam body 79 of each of the electrodes, such as the electrode 15, is sealingly bonded to the lower surface 72 of the liner 25, thus completing the seal and forming a region 102 wherein the moisture in the gel in the disk 41 is trapped and retained for a shelf life corresponding to several months. It should be noted that one aspect of our new package and electrode arrangement 5 is that each of the electrodes, such as the electrode 15 cooperates with the liner, such as the liner 25 and the sealing plastic layer 27 to produce the long term seal which retains the moisture in the electrode foam disk 41.

FIGS. 4 through 9 disclose the steps in the method of fabricating the electrode and packaging material 5.

Figure 9:
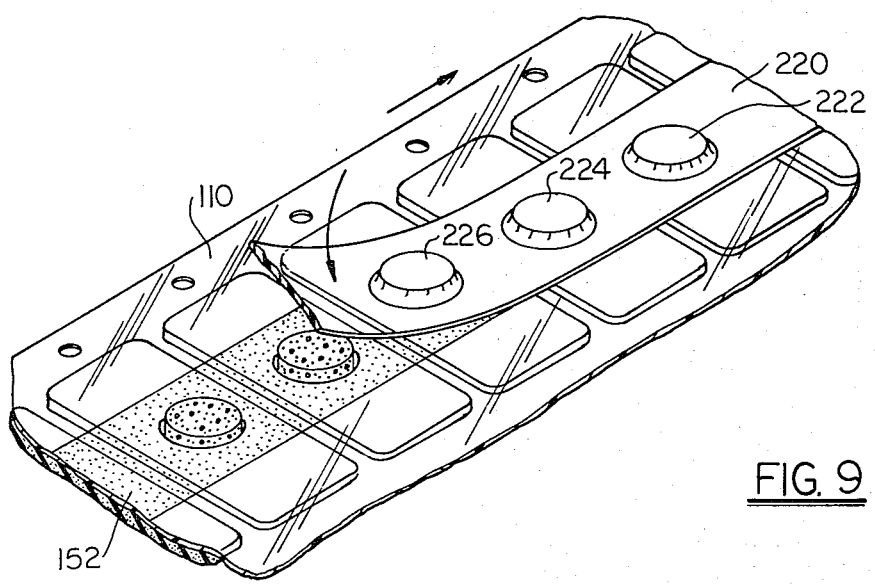
FIG. 9 is a perspective view of a fragmentary sheet of partially formed electrodes showing the step of applying a continuous, formed, plastic cover over each of the gelled disks previously applied to the strip of EKG electrodes.

In an initial step, a multi-layer pre-formed sheet 108 is prepared. This sheet includes a polyethylene base liner 110 corresponding to the previously discussed liner 25. Sealingly bonded to a lower side 112 of the polyethylene base layer 110 is a plurality of elongated foam members 114 through 122. Each of the foam members 114 through 122 corresponds to the previously discussed foam member 50. Centrally located with respect to each of the foam members 114 through 122 is a series of holes 124 through 132 in the plastic liner 110. Due to each of the holes 124 through 132 a portion 134 through 142 of the upper adhesive layer of each of the elongated foam members 114 through 122 is exposed. The polyethylene base liner has an adhesive strip applied thereto on an upper surface 150. This elongated adhesive strip 152 clearly shown in FIG. 9 is initially protected by an elongated protective liner 154 applied to the top surface 150 of the member 110. The protective liner 154 has a set of holes such as a hole 156 which corresponds to the set of holes 124 through 132 in the polyethylene base liner 110. A second protective liner 158 is applied over the first protective liner 154 and temporarily adheres to the exposed adhesive regions 134 through 142 of the elongated foam strips 114 through 122.

Starting from the multi-layer pre-form 108 shown in FIG. 4, the next step of processing involves removing the outer protective liner 158.

As shown in FIG. 5, once the outer liner 158 is removed, a series of holes, such as a hole 170 may be punched through each of the foam members 114 through 122. Each of the holes such as the hole 170 is centered with respect to the previously formed holes 124 through 132 in the polyethylene base liner 110. Any conventional punching tool such as a tool 172 suitable for punching circular holes in foam material may be used to punch the holes 170.

Figure 6:
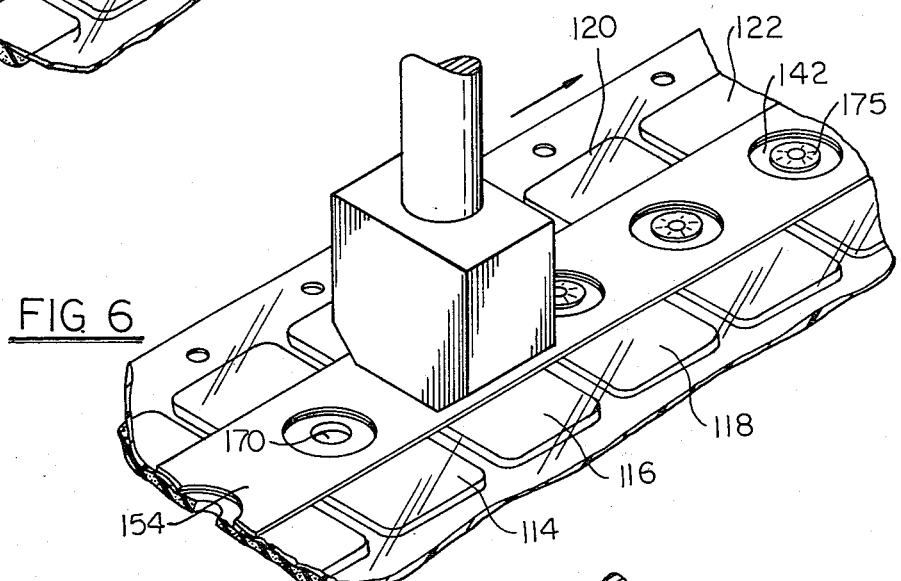
FIG. 6 is a perspective view of a fragment of the basic sheet material showing a metal contact being applied to each EKG electrode pad.

The next processing step as shown in FIG. 6 shows a two-part metal contact 175 corresponding to the contact 75 being applied to the holes, such as the hole 170 in the elongated piece of foam material such as the piece 114. Any type of one or two-part metal contact which can be applied from one side or both sides of each of the foam members 144 through 122 and which is suitable for connecting electrical instruments thereto may be used.

Figure 7:
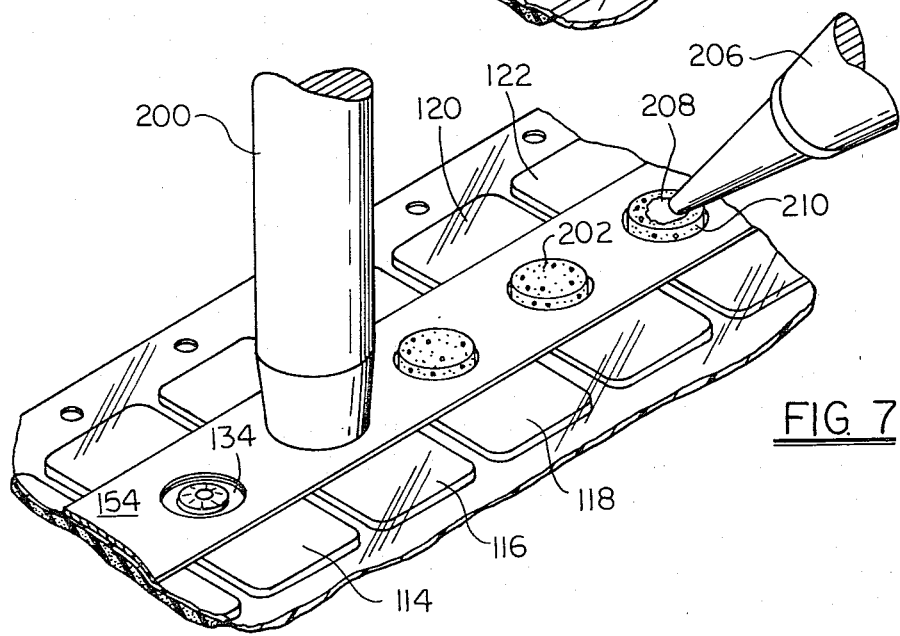
FIG. 7 is a perspective fragmentary view of a sheet of partially formed EKG electrodes showing the step of applying a foam disk to each electrode, adjacent one side of the metal contact, and the step of impregnating each said disk with gel.

FIG. 7 shows a tool 200 applying foam disks such as a foam disk 202 to each of the exposed adhesive regions 134 through 142 of each of the elongated foam members 114 through 122. FIG. 7 also shows a tool 206 injecting gel 208 into a foam disk 210 which had been previously applied to the annular adhesive region 142 left remaining once the connector 175 was applied to the elongated foam member 122. The foam disks 202, 210 adhere to the elongated foam members 114 through 122 due to the angularly shaped portion of the adhesive region 134 through 142 left exposed after the electrode contacts, such as the contact 175 have been applied to the elongated foam members 114 through 122.

Figure 8:
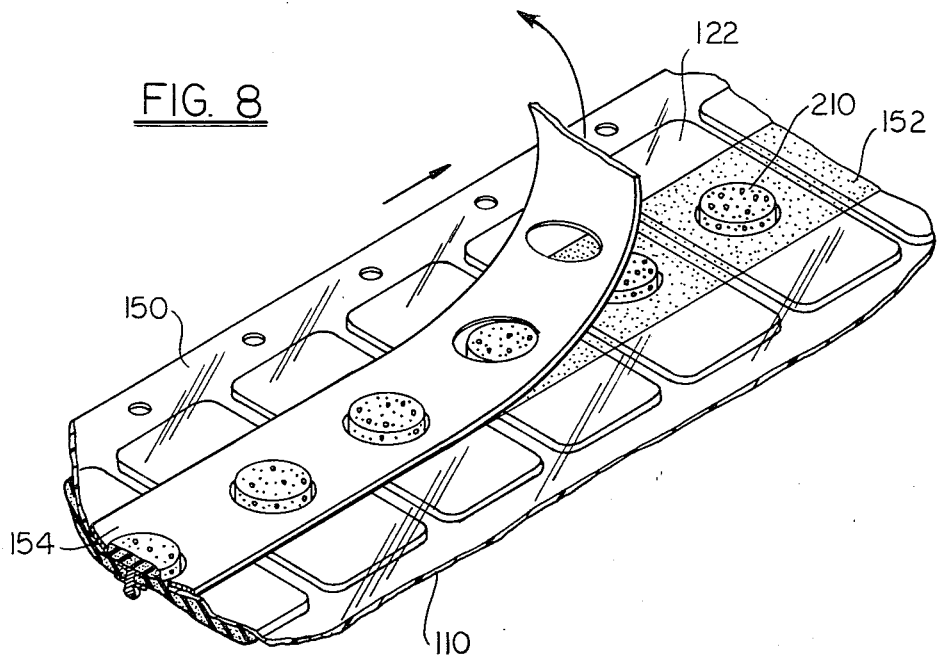
FIG. 8 is a perspective view of a fragmentary portion of a sheet of partially formed EKG electrodes showing the step of removing the remaining liner from the layer of polyethylene.

FIG. 8 shows a step of removing the protective liner 154 from the adhesive layer 152 on the top surface 150 of the polyethylene layer 110. Since the liner 154 has been removed after the gel has been applied by the applicator 206, the adhesive layer 152 has not been contaminated or otherwise damaged by the presence of any excess gel which might not have been injected completely into the disk 210.

In the last step of the process, shown in FIG. 9, a sealing layer of plastic, such as MYLAR, 220 having a plurality of caps 222 through 226 formed therein is sealingly applied to the layer of adhesive 152 and forms the remainder of the moisture proof seal with the polyethylene liner 110.

While our inventive method in FIGS. 4 through 9 has been shown being practiced with one strip of elongated foam members 114 through 122, it will be understood that the same method can be practiced with a double strip of foam members, corresponding to the structure 5 of FIG. 1.

Not only does the method shown between FIGS. 4 and 9 produce an improved packaging electrode structure 5 but because multiple rows of electrodes may be formed simultaneously, it is very inexpensive to form the electrodes and packaging 5 of our invention. The sheets of formed and packaged electrodes shown in FIG. 9 may then be cut apart as desired in the packages having predetermined numbers of electrodes. As can be seen with respect to FIG. 1, it will be appreciated that one of the advantages of our packaging arrangement 5 is that an electrode such as the electrode 21 may be readily removed from the liner 25 and conveniently used and no packaging material needs to be disposed of until all of the electrodes such as 11 through 21 have been removed from that particular piece of liner 25.

While various modifications and suggestions might be proposed by those skilled in the art, it will be understood that we wish to include all such modifications and changes within the claims of the patent warranted hereon as reasonably come within our contribution to the art.

We claim as our invention:
1. An EKG electrode and package therefor comprising:
   a rectangularly shaped foam body member with an adhesive layer affixed to a first side thereof;
   a metal contact which extends through said foam body member, is substantially centered with respect thereto and is attached only to said foam body member;
   a gel impregnated circular disk attached to said adhesive layer on said first side of said foam body member centered with respect to said metal contact;
   a selected piece of plastic sheet material with a hole therein sealingly bonded at a first side to said first side of said foam body member with said gel impregnated disk extending through said hole;
   a formed plastic cap member sealingly attached to the other side of said plastic sheet material covering said gel impregnated disk;
   a layer of selected adhesive, said layer of adhesive is located on said other side of said plastic sheet material and extends at least from a first edge of said rectangularly shaped foam body member to a second edge thereof and surrounds said hole in said plastic sheet material, and wherein
   said formed plastic cap member includes planar sealing regions, parts of said planar regions extend substantially to said first and second edges of said rectangularly shaped foam body member, said planar regions are in sealing contact with adjacent regions of said layer of adhesive,
   whereby said cap member is bonded to said other side of said plastic sheet member by said selected adhesive such that a moisture resistent seal is formed therebetween which completely surrounds a part of said disk, and
   whereby said gel impregnated circular disk is sealed within a moisture retaining region bounded by a part of said first side of said foam body member, a portion of said metal contact, a surface of said plastic sheet material which surrounds a part of said disk, a surface of said plastic cap member adjacent to said gel impregnated circular disk, and said moisture resistant seal.

2. An EKG electrode and packaging therefor comprising:
   a selected plastic sheet member having first and second pluralities of holes therethrough, each member of said first plurality of holes is spaced equidistant from at least one other member of said first plurality of holes and each member of said second plurality of holes is spaced equidistant from at least one other member of said second plurality of holes, said first and second pluralities of holes are located along first and second parallel center lines;
   a plurality of rectangularly shaped elongated foam body members, each said foam body member has a first surface with a layer of adhesive thereon and each member of said plurality of elongated foam body members is sealingly bonded to a first surface of said plastic sheet member by said layer of adhesive and centered with respect to an associated member of said first or second plurality of holes;
   a plurality of metal contacts, each member of said plurality of contacts is attached only to one of said elongated foam body members and centered with respect to said associated hole in said sheet member, a first portion of each of said contacts is centrally located adjacent said first surface of said associated elongated foam body member and a second portion which lockingly engages said first portion is located adjacent an opposite surface of said associated elongated foam body member;
   a plurality of gelled foam disks, one member of said plurality of gelled foam disks is associated with each member of said plurality of metal contacts and is attached to said first surface of said associated elongated foam body member centered with respect to said associated metal contact and extending through said associated hole in said sheet member; and
   a plurality of plastic caps, each member of said plurality of plastic caps is sealingly bonded to a second surface of said plastic sheet member, adjacent to and enclosing an associated one of said gelled disks;
   first and second elongated layers of adhesive,
   said first layer of adhesive is located on said second surface of said plastic sheet member substantially centered along said first center line of said first plurality of holes and surrounding each member of said first plurality of holes, said second layer of adhesive is located on said second surface of said plastic sheet member substantially centered along said second center line of said second plurality of holes and surrounding each member of said second plurality of holes, and wherein said plurality of plastic caps includes a connected first plurality of plastic caps with planar sealing regions in sealing contact with adjacent regions of said first layer of adhesive, said planar sealing regions adjacent each said gelled foam disk positioned along said first center line in part extend at least to first and second edges of each said respective rectangularly shaped elongated foam body member and form a plurality of moisture resistant seals each of which completely surrounds part of a respective said foam disk along said first center line, and wherein said plurality of plastic caps includes a connected second plurality of plastic caps with planar sealing regions in sealing contact with adjacent regions of said second layer of adhesive, said planar sealing regions adjacent each said gelled foam disk positioned along said second center line in part extend at least to first and second edges of each said respective rectangularly shaped elongated foam body member and form a plurality of moisture resistant seals each of which completely surrounds a part of a respective said foam disk along said second center line, whereby each said gelled foam disk is sealed within a moisture retaining region bounded by a part of said first surface of said associated foam body member, a portion of an associated one of said metal contacts, a surface of said plastic sheet member which surrounds a part of said disk, a surface of an assocated plastic cap adjacent said gelled foam disk, and an associated moisture resistant seal.

3. In an EKG electrode having a body member of a selected shape with a layer of adhesive attached to a first surface thereof, a metal contact extending through said body member, the body member being removably affixed to a first side of a base liner by the layer of adhesive, a gel impregnated foam disk attached at a first end to a selected region of the body member adjacent a portion of said metal contact and extending through a hole in the base liner, an improvement comprising:

a layer of adhesive affixed to a second side of said base liner, said layer of adhesive extends entirely across said body member completely surrounding the hole in said liner, and means for covering said hole in said base liner, said means for covering extends at least across said body member from one edge to another and is sealingly affixed to said second side of said base liner by said layer of adhesive thereby forming a moisture resistant seal which completely surrounds a part of the disk, whereby said means for covering, said base liner, said body member, said portion of said metal contact and said seal cooperate to form a moisture retaining region wherein the foam disk is positioned.

* * * * *